US00PP26227P2

(12) United States Plant Patent
Pieters et al.

(10) Patent No.: US PP26,227 P2
(45) Date of Patent: Dec. 15, 2015

(54) ***GUZMANIA* PLANT NAMED 'FLAVA'**

(50) Latin Name: *Guzmania hybrida*
Varietal Denomination: Flava

(71) Applicants: Luc Pieters, Laarne (BE); Caroline De Meyer, Laarne (BE)

(72) Inventors: Luc Pieters, Laarne (BE); Caroline De Meyer, Laarne (BE)

( * ) Notice: Subject to any disclaimer, the term of this patent is extended or adjusted under 35 U.S.C. 154(b) by 204 days.

(21) Appl. No.: 13/998,557

(22) Filed: Nov. 8, 2013

(51) Int. Cl.
*A01H 5/02* (2006.01)

(52) U.S. Cl.
USPC ..... Plt./371

(58) Field of Classification Search
USPC ..... Plt./371
See application file for complete search history.

*Primary Examiner* — Anne Grunberg
(74) *Attorney, Agent, or Firm* — C. A. Whealy

(57) ABSTRACT

A new and distinct cultivar of *Guzmania* plant named 'Flava', characterized by its compact, upright and outwardly arching growth habit; relatively broad leaves; short to intermediate inflorescences with showy yellow, orange and dark red-colored bracts; and good postproduction longevity.

2 Drawing Sheets

Botanical designation: *Guzmania hybrida.*
Cultivar denomination: 'FLAVA'.

BACKGROUND OF THE INVENTION

The present invention relates to a new and distinct cultivar of *Guzmania* plant, botanically known as *Guzmania hybrida* and hereinafter referred to by the name 'Flava'.

The new *Guzmania* plant is a product of a planned breeding program conducted by the Inventors in Laarne, Belgium. The objective of the breeding program is to create new *Guzmania* plants having unique bract colors and enhanced postproduction longevity.

The new *Guzmania* originated from a cross-pollination made by the Inventors in February, 2008 in Laarne, Belgium of *Guzmania hybrida* 'BQZ', not patented, as the female, or seed, parent with an unnamed proprietary selection of *Guzmania minor*, not patented, as the male, or pollen, parent. The new *Guzmania* plant was discovered and selected by the Inventors as a single flowering plant from within the progeny of the stated cross-pollination in a controlled environment in Laarne, Belgium in November, 2010.

Asexual reproduction of the new *Guzmania* plant by tissue culture in a controlled environment in Laarne, Belgium since December, 2010 has shown that the unique features of this new *Guzmania* plant are stable and reproduced true to type in successive generations.

SUMMARY OF THE INVENTION

Plants of the new *Guzmania* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Flava'. These characteristics in combination distinguish 'Flava' as a new and distinct *Guzmania* plant:

1. Compact, upright and outwardly arching growth habit.
2. Relatively broad leaves.

3. Short to intermediate inflorescences with showy yellow, orange and dark red-colored bracts.
4. Good postproduction longevity.

Plants of the new *Guzmania* can be compared to plants of the female parent, 'BQZ'. Plants of the new *Guzmania* differ primarily from plants of 'BQZ' in plant size as plants of the new *Guzmania* are more compact than plants of 'BQZ'. In addition, plants of the new *Guzmania* and 'BQZ' differ in bract color as plants of 'BQZ' have yellow-colored bracts.

Plants of the new *Guzmania* can be compared to plants of the male parent selection. Plants of the new *Guzmania* differ primarily from plants of the male parent selection in plant size as plants of the new *Guzmania* are taller than plants of the male parent selection. In addition, plants of the new *Guzmania* and the male parent selection differ in bract color as plants of the male parent selection have orange-colored bracts.

Plants of the new *Guzmania* can be compared to plants of *Guzmania hybrida* 'Diana', not patented. In side-by-side comparisons conducted in Laarne, Belgium, plants of the new *Guzmania* and 'Diana' differed in the following characteristics:

1. Plants of the new *Guzmania* were more compact than plants of 'Diana'.
2. Plants of the new *Guzmania* had shorter and broader leaves than plants of 'Diana'.
3. Plants of the new *Guzmania* and 'Diana' differed in bract color as plants of 'Diana' had yellow-colored bracts.
4. Bracts of plants of the new *Guzmania* retained their color longer than bracts of plants of 'Diana'.

BRIEF DESCRIPTION OF THE PHOTOGRAPHS

The accompanying colored photographs illustrate the overall appearance of the new *Guzmania* plant showing the colors as true as it is reasonably possible to obtain in colored reproductions of this type. Colors in the photographs may differ slightly from the color values cited in the detailed botanical description which accurately describe the colors of the new *Guzmania* plant.

The photograph on the first sheet comprises a side perspective view of a typical flowering plant of 'Flava' grown in a container.

The photograph on the second sheet is a top perspective view of a typical inflorescence of 'Flava'.

DETAILED BOTANICAL DESCRIPTION

The aforementioned photographs and following observations, measurements and values describe plants grown during the winter in 9-cm containers in a glass-covered greenhouse in Laarne, Belgium and under cultural practices typical of commercial *Guzmania* production. During the production of the plants, day temperatures ranged from 21° C. to 30° C., night temperatures ranged from 20° C. to 21° C. and maximum light levels were 18,000 lux. Plants were three years old when the photographs and description were taken. In the following description, color references are made to The Royal Horticultural Society Colour Chart, 2007 Edition, except where general terms of ordinary dictionary significance are used.

Botanical classification: *Guzmania hybrida* 'Flava'.

Parentage:

*Female, or seed, parent.*—*Guzmania hybrida* 'BQZ', not patented.

*Male, or pollen, parent.*—Unnamed proprietary selection of *Guzmania minor*, not patented.

Propagation:

*Type.*—By tissue culture.

*Root description.*—Thick, fleshy; creamy white in color.

*Rooting habit.*—Medium density.

Plant description:

*Plant and growth habit.*—Compact, upright and outwardly arching plant habit; broad inverted triangle; basal rosette of outwardly curved strap-like leaves affixed in tight spiral ranks; terminal inflorescence on an upright scape emerging from the center of the basal rosette; low to moderately vigorous growth habit.

*Plant height, soil surface to top of inflorescence.*—About 18.2 cm.

*Plant diameter or spread.*—About 37.4 cm.

Leaf description:

*Arrangement.*—Basal rosette, spiral phyllotaxis; leaves sessile.

*Quantity of leaves per plant.*—Plants typically produce about 24 leaves prior to inflorescence development.

*Shape.*—Ligulate.

*Apex.*—Apiculate.

*Margin.*—Entire.

*Length.*—About 22.8 cm.

*Width.*—About 3.2 cm.

*Aspect.*—Leaves curved outward over their length and arching downward towards the apex.

*Texture, upper and lower surfaces.*—Leathery, stiff; smooth, glabrous.

*Venation.*—Parallel.

*Color.*—Developing leaves, upper surface: Between 143A and 146A. Developing leaves, lower surface: Between 146B and 147B. Fully expanded leaves, upper surface: Darker than between 143A and 144A; venation, darker than between 143A and 144A. Fully expanded leaves, lower surface: Between 144A and 146B; venation, close to between 144A and 146B.

Inflorescence description:

*Inflorescence form.*—Terminal inflorescences with showy bracts; inflorescences supported on erect and strong scapes.

*Inflorescence length.*—About 18.2 cm.

*Inflorescence width.*—About 12.5 cm.

*Fragrance.*—None detected.

*Inflorescence longevity.*—Inflorescences of the new *Guzmania* are long-lasting; bract coloration is maintained for about four to five months; inflorescences persistent.

*Natural flowering season.*—Plants of the new *Guzmania* flower naturally during the winter.

*Flowers.*—Flower initiation and development have not been observed on plants of the new *Guzmania.*

*Scape.*—Length: About 10.2 cm. Diameter: About 9 mm. Strength: Strong. Aspect: Erect. Texture: Smooth, glabrous. Color: Close to 157C to 157D.

*Terminal bracts.*—Length: About 7.7 cm. Width: About 2.3 cm. Shape: Lanceolate or ligulate. Apex: Apiculate. Base: Sheathing the scape. Margins: Entire. Texture, upper and lower surfaces: Smooth, glabrous. Color: When developing, upper and lower surfaces: Close to 17C. Fully developed, upper surface: Close to 34A; towards the apex, close to 183A. Fully developed, lower surface: Close to 34A; towards the apex, close to 187A.

*Scape bracts.*—Length: About 11.9 cm. Width: About 2.7 cm. Shape: Lanceolate or ligulate. Apex: Apiculate. Base: Sheathing the scape. Margins: Entire. Texture, upper and lower surfaces: Smooth, glabrous. Color: When developing and fully developed, upper surface: Close to N144A; margins, close to 34B; towards the apex, between 143A and 146B. When developing and fully developed, lower surface: Close to 145A tinged with close to 39B; towards the apex, close to 146B.

Temperature tolerance: Plants of the new *Guzmania* have been observed to tolerate high temperatures about 40° C. and to be hardy to USDA Hardiness Zone 10.

Disease & pest resistance: Plants of the new *Guzmania* have not been observed to resistant to pathogens and pests common to *Guzmania* plants.

It is claimed:

1. A new and distinct *Guzmania* plant named 'Flava' as illustrated and described.

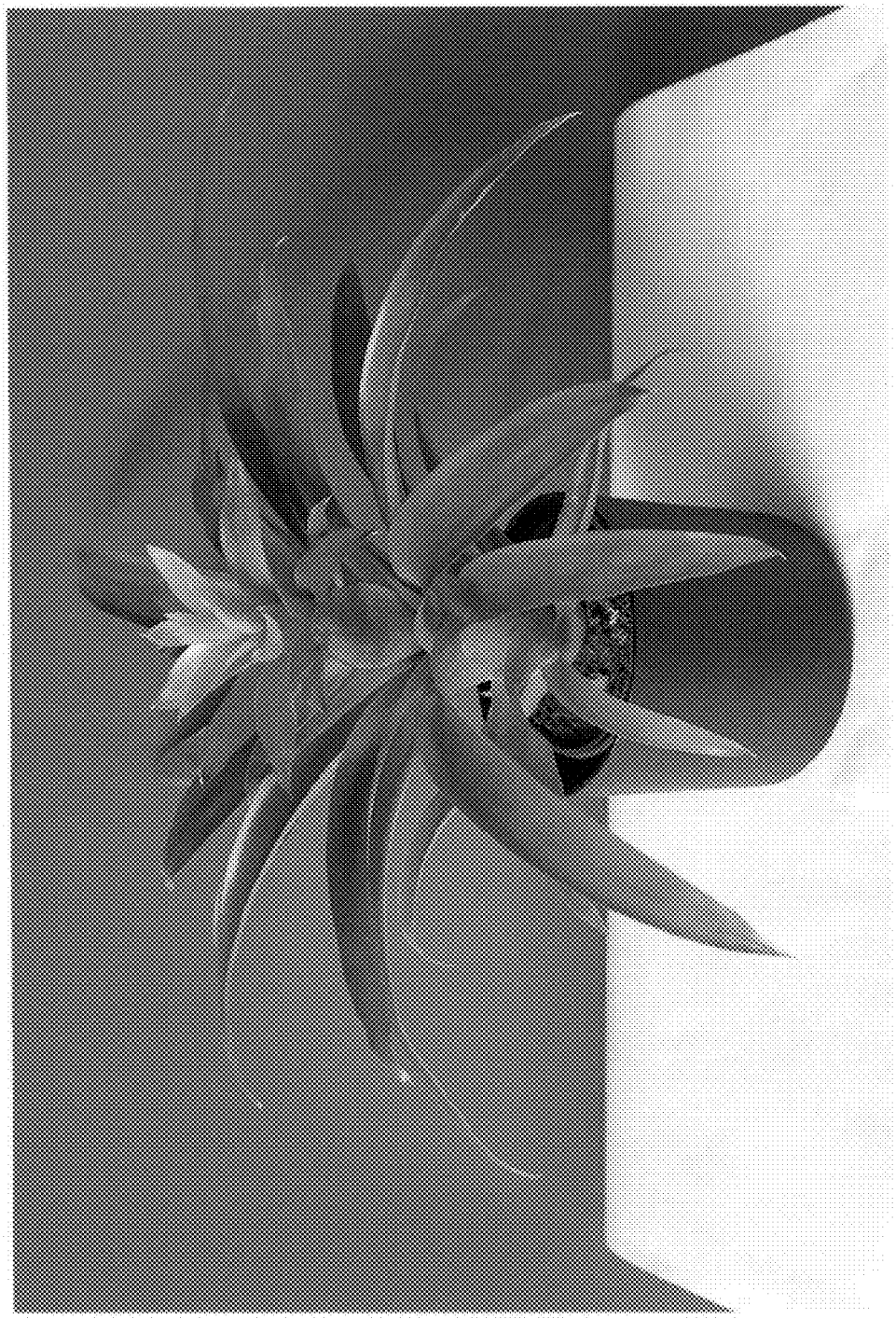

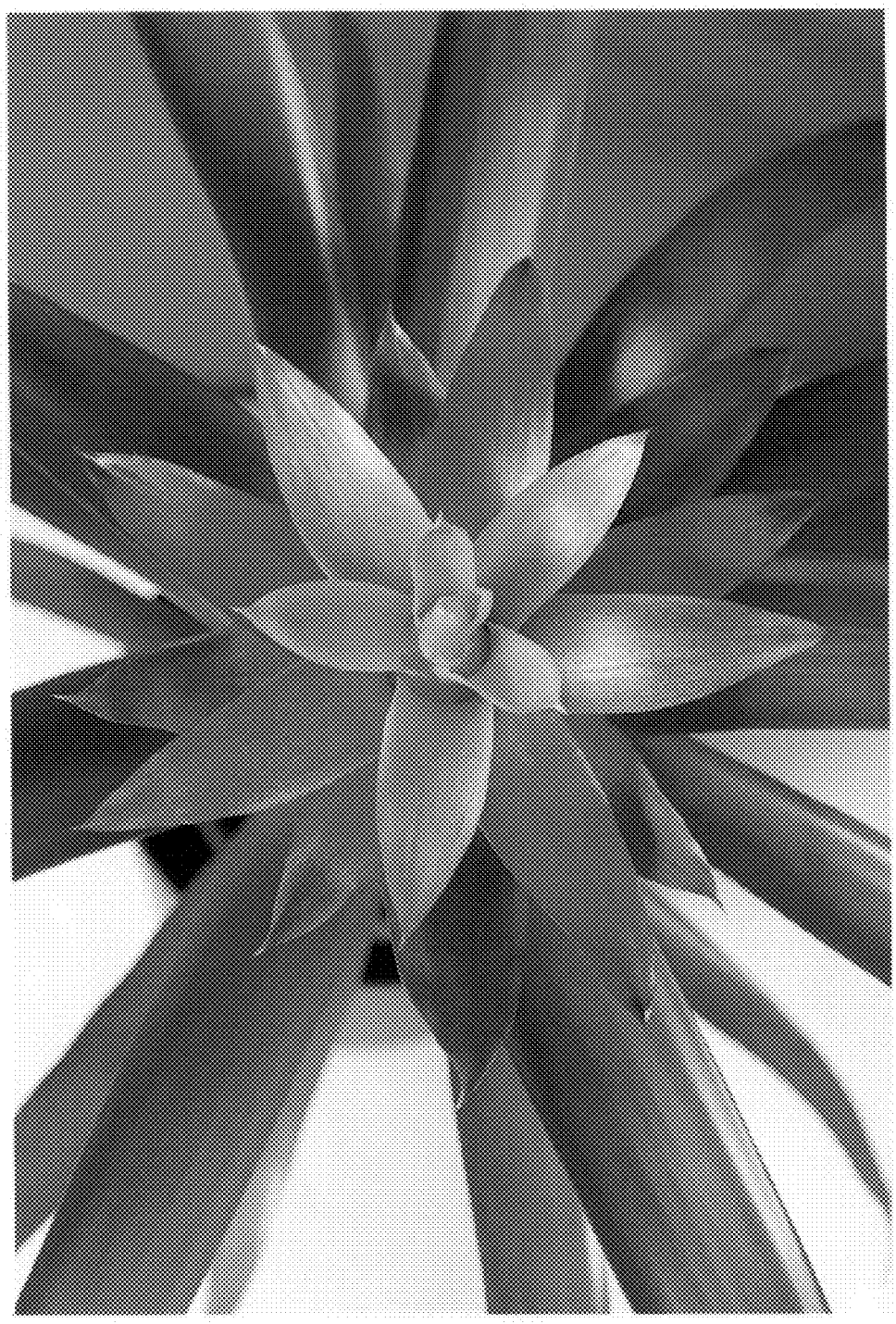

* * * * *